US010149881B2

(12) United States Patent
Lee et al.

(10) Patent No.: US 10,149,881 B2
(45) Date of Patent: Dec. 11, 2018

(54) METHOD FOR TREATING INFLAMMATORY, ALLERGIC OR ASTHMA DISEASES, CONTAINING PAPRIKA EXTRACTS

(71) Applicant: INDUSTRY-UNIVERSITY COOPERATION FOUNDATION HANYANG UNIVERSITY, Seongdong-gu, Seoul (KR)

(72) Inventors: Sang-Kyung Lee, Seoul (KR); Young-Jin You, Kimpo-shi (KR); Hyo-Sung Choi, Seoul (KR); Min-Young Park, Seoul (KR)

(73) Assignee: INDUSTRY-UNIVERSITY COOPERATION FOUNDATION HANYANG UNIVERSITY, Seongdong-gu, Seoul ( * ) Notice: Subject to any disclaimer, the term of this patent is extended or adjusted under 35 U.S.C. 154(b) by 123 days.

(21) Appl. No.: 15/052,555

(22) Filed: Feb. 24, 2016

(65) Prior Publication Data

US 2016/0263174 A1    Sep. 15, 2016

Related U.S. Application Data

(62) Division of application No. 13/636,451, filed as application No. PCT/KR2011/001951 on Mar. 22, 2011, now abandoned.

(30) Foreign Application Priority Data

Mar. 22, 2010 (KR) .............. 10-2010-25300
Mar. 21, 2011 (KR) .............. 10-2011-25017

(51) Int. Cl.
*A61K 36/00* (2006.01)
*A61K 36/81* (2006.01)
(52) U.S. Cl.
CPC .................... *A61K 36/81* (2013.01)
(58) Field of Classification Search
CPC ........................................... A61K 36/00
See application file for complete search history.

(56) References Cited

U.S. PATENT DOCUMENTS

| 2004/0175785 A1 | 9/2004 | Kanner et al. |
| 2008/0103102 A1 | 5/2008 | Belgorod |
| 2008/0113076 A1 | 5/2008 | Klingenberg |

FOREIGN PATENT DOCUMENTS

| JP | 02207023 A | * | 8/1990 |
| JP | H11-236334 A | | 8/1999 |
| JP | 2002-308792 A | | 10/2002 |
| JP | 2003-206225 A | | 7/2003 |
| KR | 2002025152 A | * | 4/2002 |
| KR | 20100064816 A | | 6/2010 |
| WO | WO 00/33855 A1 | | 6/2000 |
| WO | WO 2011/048221 A1 | | 4/2011 |

OTHER PUBLICATIONS

F. Takano, "Capsicum ethanol extracts and capsaicin enhance interleukin-2 and interferon-gamma production in cultured murine Peyer's patch cells ex vivo," Life Sciences, 2007, vol. 80, pp. 1553-1563.
Hyuck-Se Kwon et al., "Antiinflammatory effect of acqueous extract from red peppers on lipopolysacchairide induced inflammatory resonses in murine macrophages," Journal of Korean Society of Food Science and Nutrition, 2009, vol. 30, No. 10, pp. 1289-1294.
K. Aizawa et al., "Dietary capsanthin, the main carotenoid in paprika (*Capsicum annuum*), alters plasma high-density lipoprotein-cholesterol levels and hepatic gene expression in rats," British Journal of Nutrition, 2009, vol. 102, pp. 1760-1766.
Khan Mohammad Azam, Muheet Azam, vol. 4, No. 3, pp. 4-8 (1895).
Khan Mohammad Najmul Ghani, Khazaain-al-Advia, vol. 2, pp. 9-13 (1911).
Mi Hee Yue et al., "Induction of quinine reductase activity in hepatoma cells by Paprika (*Capsicum annuum* L.)," Korean Journal of Food Science and Technology, 2006, vol. 38, No. 5, pp. 707-711.
Mudaliar Kandasamy, Aavialikkum Amuthamurai Churukkam (Athmarakshaamirtha Vaithiya saarasangiraham), vol. 1, pp. 14-18 (1975).
Rina Yu et al., "Effect of dietary hot red pepper powder on humoral immune response in rat," Journal of Korean Society of Food Science and Nutrition, 1995, vol. 24, No. 6, pp. 837-842.
Barnes et al., "Inflammatory Mediators of Asthma: An Update," Pharmacological Reviews, 1998, vol. 50(4), pp. 515-596.
Communication Pursuant to Rule 114(2) EPC issued in European Patent Application No. 11759706.2 dated May 21, 2014 (14 pages).
Communication Pursuant to Rule 114(2) EPC issued in European Patent Application No. 11759706.2 dated Mar. 27, 2015 (11 pages).
Das et al., "Luteolin alleviates bronchoconstriction and airways hyperreactivity in ovalbumin sensitized mice," Inflamm. res. vol. 52, 2003, pp. 101-106.
Database Accession No. 1999-544938, XP-002702916, dated Aug. 31, 1999 (2 pages).
Database Accession No. 2010-H31540, XP-002702915, dated Jun. 15, 2010 (2 pages).
Deepa et al., "Antioxidant constituents in some sweet pepper (*Capsicum annuum* L.) genotypes during maturity," LWT, vol. 40, 2007, pp. 121-129.
Formula ID EA1B/90G, "Key Attributes of TKDL," 1872, pp. 9-10.
Formula ID EA1B/90H, "Key Attributes of TKDL," 1872, pp. 18-20.

(Continued)

*Primary Examiner* — Qiuwen Mi
(74) *Attorney, Agent, or Firm* — Arent Fox LLP

(57) ABSTRACT

The present invention relates to a composition containing a paprika extract as an active ingredient, and more particularly to a pharmaceutical composition or health functional food for preventing or treating inflammatory, allergic or asthma disease, which contains a paprika extract. Particularly, paprika is a natural food which is readily available to anyone, and thus does not cause adverse effects even when it is taken for a long period of time.

8 Claims, 16 Drawing Sheets

(56) References Cited

OTHER PUBLICATIONS

Formula ID JA6/741Y, "Key Attributes of TKDL," 1926, pp. 10-11.
Formula ID RS23/1119, "Key Attributes of TKDL," 1998, pp. 12-17.
Galli et al., "Mast-cell-leukocyte cytokine cascades in allergic inflammation," Allergy, 1995, vol. 50, pp. 851-862.
Hee et al., "Impact of oxidative stress of lung diseases," Respirology, 2009, vol. 14, pp. 27-38.
Howard et al., "Changes in Phytochemical and Antioxidant Activity of Selected Pepper Cultivars (*Capsicum* Species) as Influenced by Maturity," J. Agric. Food Chem., 2000, vol. 48, pp. 1713-1720.
Jang et al., "*Capsicum annuum* L. Methanolic Extract Inhibits Ovalbumin-Induced Airway Inflammation and Oxidative Stress in a Mouse Model of Asthma," Journal of Medicinal Food, vol. 14, 2011, pp. 1144-1151.
Motohashi et al., "Cytotxic and Multidrug Resistance Reversal Activity of a Vegetable, 'Anastasia Red' a Variety of Sweet Pepper," Phytotherapy Research, vol. 17, 2003, pp. 348-352.
Neuman et al., "Prevention of exercise-induced asthma by a natural isomer mixture of Beta-carotene," Ann. Allergy Asthma Immunol., 1999, vol. 82, pp. 549-553.
Office Action issued in European Patent Application No. 11759706.2 dated Jul. 25, 2014 (7 pages).
Office Action issued in European Patent Application No. 11759706.2 dated Oct. 8, 2015 (6 pages).
Park et al., "Quercetin regulates Th1/Th2 balance in a minute model of asthma," International Immunopharmacology, vol. 9, 2009, pp. 261-267.
Riccioni et al., "Minireview: Antioxidant Vitamin Supplementation of Asthma," Annals of Clinical & Laboratory Science, vol. 37(1). 2007, pp. 96-101.
Shirataki et al., Bioactivities of Anastasia Black (Russian Sweet Pepper), Anticancer Research, vol. 25, 2005, pp. 1991-2000.
Sun et al., "Antioxidant Activities of Different Colored Sweet Bell Peppers (*Capsicum annuum* L.)," Journal of Food Science, vol. 72, 2007; pp. 98-102.
Supplemental European Search Report issued in European Patent Application No. EP11759706 dated Jul. 17, 2013 (9 pages).

\* cited by examiner 12-hr exposure 24-hr exposure

METHOD FOR TREATING INFLAMMATORY, ALLERGIC OR ASTHMA DISEASES, CONTAINING PAPRIKA EXTRACTS

CROSS REFERENCE TO RELATED APPLICATION

This application is a Divisional of U.S. patent application Ser. No. 13/636,451 filed Nov. 26, 2012, which is a 35 U.S.C 371 National Phase Application No. PCT/KR2011/001951 filed Mar. 22, 2011, which claims priority to Korean Patent Application Nos. KR-10-2010-25300filed Mar. 22, 2010 and KR-10-2011-25017 filed Mar. 21, 2011. The disclosure of these prior applications are hereby incorporated in their entirety by reference.

TECHNICAL FIELD

The present invention relates to a pharmaceutical composition or health functional food for preventing or treating inflammatory, allergic or asthma disease, which contains a paprika extract as an active ingredient.

BACKGROUND ART

Oxidative stress is known to be closely related to aging and various diseases. Particularly, oxidative stress is known to be closely related to autoimmune responses, and examples of diseases caused by oxidative stress include inflammatory reactions, such as asthma, allergy, atopy and nasitis.

As is known, respiratory disease patients show an imbalanced ratio of oxidants to antioxidants, and superoxide dismutase (SOD), a peroxide inhibitor, relieves respiratory diseases. It was also reported that antioxidants can be used to treat inflammatory reactions caused by oxidative stress. In addition, it is known that reactive oxygen species (ROS) cause immune system abnormalities and autoimmune diseases and increase the expression of interleukin-4 (IL-4) and interleukin-13 (IL-13).

Interleukin-4 and interleukin-13 are cytokines made by T-helper 2 cells (Th2 cells) and are very closely related to autoimmune diseases. In signaling of these interleukins, Janus-associated kinase (JAK), STATE, IRS 1/2, phosphoinositol-3 kinase (PI-3 kinase) and the like are involved and cause proinflammatory cytokines, including interleukin-1, interleukin-6, interleukin-8, interleukin-10, interleukin-12 and the like. In addition, interleukin-4 and interleukin-13 are involved in the expression of immunoglobulin IgE, MHC class II antigen, and cluster of differentiation (CD23) and the proliferation of B cells and are also closely related to the differentiation of T helper 2 cells.

Particularly, bronchial asthma is a chronic allergic inflammatory disease in bronchi. Bronchial asthma occurs when the bronchial airways have inflammation or the bronchi have an increased sensitivity to allergens. It also occurs when the airway muscles become thicker or swell.

Asthma is caused by external factors or internal factors. The external factors include atmospheric pollutants, various allergens and industrial particles. These asthma triggers produce IgE in immune responses, and the produced IgE clogs the nasal, skin and airway passages and binds to receptors on the surface of mast cells in various organs to cause inflammation. The internal factors include genetic factors. It is known that human chromosome 5, 32-adrenoreceptor gene and human chromosomes 11, 12, 14 and 16 are involved in the occurrence of asthma and the changes in these genes increase IgE and cause hypersensitivity.

In asthma symptoms, CD4+ T cells in the airway are controlled, and upon exposure to triggering allergens, airway inflammation occurs which is characterized by an increase in Th2 immune responses, the inhibition of Th1 immune responses and the infiltration of eosinophils. Thus, various inflammatory cells, including eosinophils, neutrophils and lymphocytes, infiltrate bronchial mucosa and alveoli, and the kind and amount of cytokine secreted change. Therapies for controlling immune responses in bronchial asthma include avoidance therapy for allergens, and desensitization therapy for allergies, but it is actually impossible to avoid allergens.

Also, existing desensitization therapies that use steroids, β2-agonists and cromones are limited to patients with atopic bronchial asthma caused by some allergens and can cause serious adverse effects such as anaphylaxis. In addition, the development of asthma therapeutic agents, such as soluble IL-4 receptors and soluble IL-13 and anti-IL-5 antibodies, which use mechanisms for inhibiting the action of Th2-type cytokines, is in progress. However, many agents for treating asthma are available only on a physician's prescription and are mostly steroidal drugs which can cause adverse effects upon long-term use.

Accordingly, the present inventors have made extensive efforts to develop a pharmaceutical composition or food effective for the treatment of inflammatory, allergic or asthma disease, which is based on a food readily available to anyone and does not cause side effect even upon long-term use. As a result, the present inventors have found that an extract of paprika is effective for the treatment of the above disease, thereby completing the present invention.

DISCLOSURE OF INVENTION

Technical Problem

It is a main object of the present invention to provide a pharmaceutical composition for preventing or treating inflammatory, allergic or asthma disease, which contains a paprika extract as an active ingredient.

Another object of the present invention is to provide a health functional food for preventing or ameliorating inflammatory, allergic or asthma disease, which contains a paprika extract and food-acceptable additives.

Technical Solution

To achieve the above objects, the present invention provides a pharmaceutical composition for preventing or treating inflammatory, allergic or asthma disease, which contains a paprika extract as an active ingredient.

The "inflammatory, allergic or asthma disease" may be one or more diseases selected from the group consisting of acute inflammation, chronic inflammation, bronchitis, bronchial asthma, allergic nasitis, allergic asthma, allergic dermatitis, and atopy, and typical examples thereof include bronchial asthma, allergic natitis, atopy and the like.

In the present invention, the extract may be a crude extract, polar solvent-soluble extract or non-polar solvent-soluble extract of paprika.

Herein, the crude extract is preferably an extract solubilized in a solvent selected from among water, including purified water, methanol, ethanol, butanol, and mixed solvents thereof. The polar solvent-soluble extract is preferably an extract solubilized in a solvent selected from among water, ethanol, butanol, and mixed solvents thereof. The non-polar solvent-soluble extract is preferably an extract solubilized in hexane, chloroform, dichloromethane or ethyl acetate.

Further, the content of the paprika extract in the composition is preferably 0.1-50 wt % based on the total weight of the composition. The paprika that is used in the present invention may be, for example, green, orange, yellow or red in color.

The present invention also provides a health functional food for preventing or ameliorating inflammatory, allergic or asthma disease, which contains a paprika extract as an active ingredient.

In the present invention, the health functional food may be used, for example, in the form of powders, granules, tablets, capsules, syrups, or beverages. The content of the paprika extract in the health functional food may be 0.01-15 wt % based on the total weight of the food.

The composition containing the paprika extract according to the present invention is effective for the prevention or treatment of oxidative stress-induced inflammatory responses, such as inflammation, allergy or asthma. Particularly, paprika is a natural food which is readily available to anyone, and thus does not cause adverse effects even when it is taken for a long period of time.

BEST MODE FOR CARRYING OUT THE INVENTION

Figure 1:
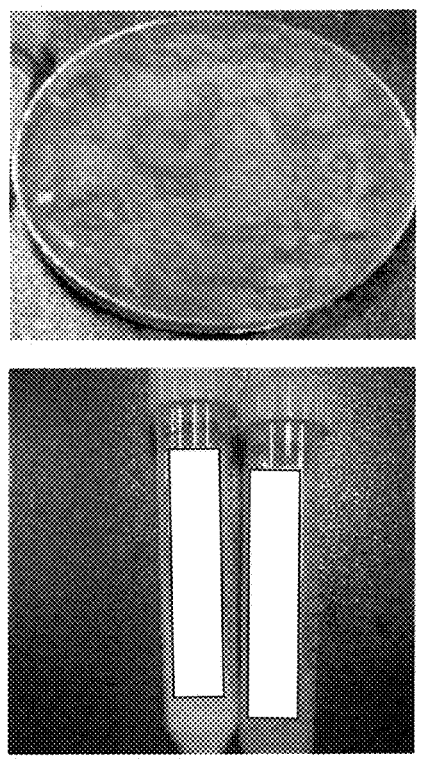
FIG. 1 is a photograph of a paprika extract powder prepared from paprika.

The definitions of the terms used in the present invention are as follows.

The "extract" that is used in the present invention may be a crude extract, a polar solvent-soluble extract or non-polar solvent-soluble extract of paprika.

As used herein, the term "crude extract" is meant to include an extract solubilized in a solvent selected from among water, including purified water, lower alcohols containing 1 to 4 carbon atoms, such as methanol, ethanol or butanol, and mixed solvents thereof, preferably a mixed solvent of water and ethanol, and more preferably a 50-100% ethanol.

As used herein, the term "polar solvent-soluble extract" is meant to include an extract solubilized in a solvent selected from among water, methanol, butanol, and mixed solvents thereof, preferably water or butanol, and more preferably butanol.

As used herein, the term "non-polar solvent-soluble extract" is meant to include an extract solubilized in a hexane, chloroform, dichloromethane or ethyl acetate solvent, preferably a hexane, dichloromethane or ethyl acetate solvent, and more preferably a hexane or ethyl acetate solvent.

As used herein, the term "pharmaceutical composition" refers to a mixture of the paprika extract and other chemical components such as diluents or carriers.

As used herein, the term "carrier" is defined as a compound that facilitates the incorporation of a compound into cells or tissues. For example, dimethylsulfoxide (DMSO) is a carrier which is commonly used to facilitate the incorporation of many organic compounds into the cells or tissues of organisms.

As used herein, the term "diluent" refers as a compound diluted in water that will dissolve the compound of interest as well as stabilize the biologically active form of the compound. Salts dissolved in buffered solution are generally used as diluents as in the art. One commonly used buffered solution is phosphate buffer saline because it mimics the salt conditions of human blood. Since buffer salts can control the pH of a solution at low concentrations, a buffered diluent rarely modifies the biological activity of a compound.

As used herein, the term "subject" or "patient" means any single subject for which therapy is desired, including humans, cattle, dogs, guinea pigs, rabbits, chickens, insects and so on. Also intended to be included as a subject are any subjects involved in clinical research trials not showing any clinical sign of disease, or subjects involved in epidemiological studies, or subjects used as controls. In one embodiment of the present invention, the subject is a human.

As used herein, the term "tissue or cell sample" means a collection of similar cells obtained from a tissue of a subject or patient. The source of the tissue or cell sample may be solid tissue as from a fresh, frozen and/or preserved organ or tissue sample or biopsy or aspirate; blood or any blood constituents; or cells from any time in gestation or development of the subject. The tissue sample may also be primary or cultured cells or cell lines.

Optionally, the tissue or cell sample is obtained from a primary or metastatic tumor. The tissue sample may contain compounds which are not naturally intermixed with the tissue in nature such as preservatives, anticoagulants, buffers, fixatives, nutrients, antibiotics, or the like. For the purposes herein, a "section" of a tissue sample is meant a single part or piece of a tissue sample, e.g. a thin slice of tissue or cells cut from a tissue sample. It is understood that multiple sections of tissue samples may be taken and subjected to analysis according to the present invention, provided that it is understood that the present invention comprises a method whereby the same section of tissue sample is analyzed at both morphological and molecular levels, or is analyzed with respect to both protein and nucleic acid.

As used herein, the term "effective amount" is an amount sufficient to effect beneficial or desired clinical or biochemical results. An effective amount can be administered one or more times. For purposes of this invention, an effective amount of an inhibitor compound is an amount that is sufficient to palliate, ameliorate, stabilize, reverse, slow or delay the progression of the disease state. A composition is said to be "pharmacologically acceptable" if its administration can be tolerated by a recipient patient. Such an agent is said to be administered in a "therapeutically effective amount" if the amount administered is physiologically significant. An agent is physiologically significant if its presence results in a detectable change in the physiology of a recipient patient.

The term "treating", as used herein, unless otherwise indicated, means reversing, alleviating, or inhibiting the progress of, the disorder or condition to which such term applies, or one or more symptoms of such disorder or condition. The term "treatment", as used herein, refers to the act of treating as "treating" is defined immediately above.

As used herein, the term "functional food" refers to a food obtained by adding the paprika extract of the present invention to general food so as to improve the functionalities of the general food. Functionalities can be broadly divided into physical properties and physiological functionalities, and when the paprika extract of the present invention to general food, the physical properties and physiological functionalities of the general food will be improved. In the present invention, such food having improved functions is generally defined as "functional food".

Hereinafter, the present invention will be described in detail.

Unless defined otherwise, all technical and scientific terms used herein have the same meaning as commonly understood by one of ordinary skill in the art to which this invention belongs. Although desired methods and materials are described herein, any methods and materials similar or equivalent to those described herein also fall within the scope of the present invention. The contents of all the publications described by reference herein are incorporated into the present invention.

In one aspect, the present invention is directed to a pharmaceutical composition for preventing or treating inflammatory, allergic or asthma disease, which contains a paprika extract as an active ingredient.

That is, the present invention is directed to a composition for preventing or treating inflammatory, allergic or asthma disease.

The "inflammatory, allergic or asthma disease" is meant to include acute inflammation, chronic inflammation, bronchitis, bronchial asthma, atopy, allergic nasitis, allergic asthma or allergic dermatitis, preferably acute inflammation, chronic inflammation, bronchial asthma, allergic nasitis or allergic asthma, and more preferably bronchial asthma, atopy or allergic nasitis.

More specifically, the effect of preventing or treating inflammatory, allergic or asthma disease as defined herein means the effect of inhibiting COX-2-dependent PGD2 production and the production of IL-4, IL-5 and LTC4. Thus, although asthma disease is described as a typical example in an embodiment of the present invention, the asthma disease can be said to be representative of inflammation, allergy and the like which are characterized by the above-described mechanism.

Asthma is a chronic inflammatory disease caused by typical inflammatory cells, such as mast cells, and various humoral inflammatory mediators such as eosinophils and T-lymphocytes and is characterized by airway obstruction and bronchial hypersensitivity, and various mediators are involved in the pathology thereof. Substances which are known to be involved in asthma include leukotriene (LT) C4, D4 and E4, which are the metabolic products of 5-lipoxygenase known as SRS-A (slow reacting substance of anaphylaxis), as well as interleukin (IL)-4, -5 and -6 which are inflammatory cytokines (Barnes P. J, et al., Inflammatory mediators of asthma: an update, Pharmacol Rev, 50, pp 515-596, 1998; Galli S, et al., Mast-cell-leukocyte cytokine cascades in allergic inflammation, Allergy 50, pp 851-862, 1995).

Asthma is a disease caused by a kind of inflammatory response, and inflammation is a defensive response to tissue injury in a local area of the body. That is, the inflammatory response is a defense response that removes injury caused by various harmful stressors to restore the tissue to the original state. Inflammatory stressors include infections or physical and chemical stressors, and biological factors related to inflammatory responses include low-molecular or high-molecular weight chemical substances, such as free radicals, proteins, saccharides or lipids, as well as plasma, blood cells, blood vessels and connective tissues. The processes of inflammation can be divided into acute inflammation and chronic inflammation. Acute inflammation is a short-term (within several days) response in which plasma components or blood cells are involved in the removal of foreign substances through the micro-circulatory system. Chronic inflammation is long-lasting and shows tissue proliferation or the like.

Antigenic substances that cause allergy are referred to as allergens. When an allergen enters the body through the respiratory organ or the skin, an IgE antibody specific for the allergen is produced and attached to the surface of allergy-causing cells. When the allergen enters the body again, it binds to the IgE antibody on the surface of the allergy-causing cells, and the stimulated allergy-causing cells release various mediators, including histamines, after which a variety of inflammatory cells, including eosinophils, are introduced into the allergy-causing cells, thus causing inflammatory responses. A key mediator that induces the inflammatory and allergic diseases is produced from the precursor arachidonic acid by phospholipases A2, such as prostaglandins, leukotriens and platelet-activating factor (PAF), cyclooxygenase and lipoxygenase.

Prostaglandins serve to bind to a specific cell surface receptor to increase the intracellular concentration of cAMP (cGMP in some cases). The effects resulting from the increase in cAMP concentration vary depending on the kind of cell, and it is known that PGA2 and PGB2 lower blood pressure and PGD2 and PGEI are involved in inflammation processes, such as pain and fever. Particularly, PGD2 is known as a main factor that worsens asthma by contracting the smooth muscle of bronchial asthma patients.

Leukotriens (LTs) constitute a group of locally functional hormones produced from arachidonic acid in vivo, and major leukotrienes include leukotriene B4 (LTB4), C4 (LTC4), D4 (LTD4) and E4 (LTE4). The biosynthesis of these leukotrienes involves the production of an epoxide known as leukotriene A4 (LTA4) from arachidonic acid by the action of 5-lipoxygenase, and LTA4 is then converted to other leukotrienes (LTB4, LTC4, LTD4 and LTE4) through a series of enzymatic steps. Leukotriens are known to be involved in pulmonary arterial diseases, for example, asthma, chronic bronchitis and related obstructive airway diseases, allergy and allergic responses, such as allergic nasitis, contact dermatitis or allergic conjunctivitis, and inflammations, such as arthritis, inflammatory bowel diseases or pain. Drugs which have recently received attention as agents for treating allergic asthma are drugs having activities of inhibiting the release of histamines, the production of leukotrien C4 and the production of platelet-activating factor.

The composition of the present invention contains a paprika extract as an active ingredient so as to prevent or treat inflammatory, allergic or asthma disease.

Paprika is an annual plant having a scientific name of '*Capsicum annuum* var. *angulosum*' and belonging to the *annuum* species of the *Capsicum* genus of the Solanaceae family. Paprika has six subtypes, and the word "paprika" is derived from Greece and collectively refers to all kinds of pepper in European. Paprika is known as a health food which contains carotenoid pigments, such as capsanthin, β-cryptoxanthin and zeaxanthin, and is rich in vitamins A, B1 and C. In addition, paprika contains large amounts of luteolin, pectin, capsaicin and the like. It is green, red, yellow or orange in color according to the pigment contained therein.

The paprika extract can be prepared by a method known in the art, a modified method thereof or the method of the present invention.

In one embodiment, the paprika extract can be prepared by the following method.

The extract or crude extract of paprika of the present invention can be prepared in the following manner. Paprika is added to an about 1-30-fold volume (preferably 5-15-fold volume) (w/v) of a solvent selected from among water, including purified water, lower alcohols having 1 to 4 carbon atoms, such as methanol, ethanol or butanol, and mixed solvents thereof, preferably a mixed solvent of water and ethanol, more preferably 50-100% ethanol, and is extracted about 1-7 times, preferably 1-3 times, at about 0 to 100° C., preferably room temperature, for 10-60 hours, preferably 30-50 hours, by an extraction method such as maceration extraction (cold extraction), hot-water extraction, ultrasonic extraction, or heating extraction, preferably maceration extraction. The extract is concentrated under reduced pressure, thereby obtaining the paprika extract of the present invention.

In addition, the polar solvent-soluble or non-polar solvent-soluble extract of the present invention can be prepared in the following manner. The crude extract obtained as described above, preferably the 50-100% ethanol crude extract, is dispersed in an about 1-150-fold volume (preferably 5-100-fold volume) (w/v) of water, and then hexane, ethyl acetate and butanol are sequentially added thereto in an amount of about 1-10 times (preferably 1-5 times) the volume of the water, and the crude extract is fractionated 1-5 times, preferably 2-4 times, thereby obtaining the polar solvent-soluble or non-polar solvent-soluble extract of the present invention.

Thus, in another aspect, the present invention is directed to a method of preparing said paprika extract. The above preparing method is merely illustrative, and can be used by properly making a modification using various methods based on the technology related in the art to which the present invention pertains. For example, the non-illustrated extraction method according to can be successfully performed by a person of an ordinary skill in the art through a distinct modification.

The detailed reaction conditions for preparation of the paprika extract according to the present invention can be understood by a person having an ordinary skill in the art through the preparation examples and examples, which will be described later, and thus the detailed description thereof will be omitted to avoid redundancy.

A pharmaceutical composition for preventing or treating inflammatory, allergic or asthma disease, which contains the inventive paprika extract obtainable by the above-described method, contains the extract in an amount of 0.1-50 wt % based on the total weight of the composition.

The pharmaceutical composition containing the paprika extract of the present invention may further comprise suitable carriers, excipients, and diluents, which are typically used in the preparation of the pharmaceutical composition.

In addition, the composition containing the paprika extract of the present invention may be formulated or used in combination with known drugs, such as steroidal drugs, antihistamine agents, anti-inflammatory drugs and antibiotics.

The pharmaceutical composition containing the paprika extract according to the present invention can be formulated according to a conventional method. For example, it may be formulated in the form of powders, granules, tablets, capsules, suspensions, emulsions, syrups, aerosols, agents for external applications, suppositories, and sterile injection solutions.

Carriers, excipients and diluents that can be contained in the composition containing the paprika extract according to the present invention include lactose, dextrose, sucrose, sorbitol, mannitol, xylitol, erythritol, maltitol, starch, gum acacia, alginate, gelatin, calcium phosphate, calcium silicate, cellulose, methyl cellulose, microcrystalline cellulose, polyvinylpyrrolidone, water, methylhydroxybenzoate, propylhydroxybenzoate, talc, magnesium stearate, and mineral oil.

For formulations, commonly used diluents or excipients such as fillers, expanders, binders, wetting agents, disintegrants and surfactants, etc., are used.

Solid Formulations for oral administration include tablets, pills, powders, granules, capsules, etc. Such Formulations are prepared by mixing the paprika extract of the present invention with at least one excipient, such as starch, calcium carbonate, sucrose, lactose, gelatin, etc. In addition to simple expedients, lubricants such as magnesium stearate, talc, etc. may also be added. Liquid Formulations for oral administration, such as suspensions, internal solutions, emulsions, syrups, etc., may comprise simple diluents, e.g., water and liquid paraffin, as well as various excipients, e.g., wetting agents, sweeteners, aromatics, preservatives, etc.

Formulations for parenteral administration include sterilized aqueous solutions, non-aqueous solvents, suspensions, emulsions, lyophilized agents, suppositories, etc. Non-aqueous solvents and suspensions may be prepared using propylene glycol, polyethylene glycol, vegetable oils such as olive oil, or injectable esters such as ethyloleate. As a base for suppositories, Witepsol, Macrogol, Tween 61, cacao fat, laurin fat, glycerogelatin, etc. may be used.)

The dosage of the paprika extract of the present invention may vary depending on the patient's age, sex and weight, but it may be administered at a dosage of 0.0001-100 mg/kg, preferably 0.001-10 mg/kg, once or several times a day. In addition, the dosage of the paprika extract can be increased or decreased depending on the route of administration, severity of the disease, the patient's sex, weight, and age, and the like. Thus, the dosage is not intended to limit the scope of the present invention in any way.

The pharmaceutical composition of the present invention may be administered by various routes to mammals, including rats, mice, livestock and humans. All routes of administration can be contemplated and include, for example, oral, tissue, rectal, intravenous, intramuscular, intrauterine, intrathecal or intracerebrovascular injections.

The pharmaceutical composition of the present invention may be used in the form of pharmaceutically acceptable salts and may be used alone or in combination with other pharmaceutically active compounds.

The present invention is characterized in that the pharmaceutical composition containing the paprika extract is effective for the treatment of inflammatory, allergic or asthma disease.

Particularly, the excellent effect of the inventive paprika extract on the inhibition of inflammatory, allergic or asthma disease can be said to be an effect attributable to a combination of various components present in the paprika extract. Whether the asthma inhibitory effect of the paprika extract of the present invention is attributable to various components or a specific component alone was examined in the Examples of the present invention. As a result, it was shown that the specific component luteolin did not reduce blood immunoglobulin-E (IgE) levels and showed an effect similar to that of budesonide which has been used as an asthma-relieving agent.

In other words, a combination of various components present in the paprika extract shows the effect of reducing blood immunoglobulin-E (IgE) levels, and the effect of the specific component luteolin alone on asthma inhibition is not excellent.

In the meantime, in still another aspect, the present invention is directed to a health functional food for preventing or ameliorating inflammatory, allergic or asthma disease, which contains a paprika extract as an active ingredient.

Functionalities can be broadly divided into physical properties and physiological functionalities, and when the paprika extract of the present invention to general food, the physical properties and physiological functionalities of the general food will be improved. For example, based on the effect of the inventive paprika extract on the inhibition of asthma, allergy, atopy or nasitis, a functional food for preventing or ameliorating inflammation, allergy, atopy or asthma can be prepared. In addition, a food having enhanced functionality can be prepared.

In addition, a compound containing the inventive paprika extract or a pharmaceutically acceptable salt thereof can be used as a main component, an additive or an adjuvant in the preparation of various functional foods and health functional foods.

Examples of foods to which the inventive paprika extract can be added include various foods, powders, granules, tablets, capsules, syrups, drinks, gums, vitamin complexes, and health functional foods.

In one embodiment, the extract of the present invention may be added to a food or drink for preventing asthma or allergic disease. With respect to the content of the extract in a food or a drink, the extract of the present invention may be added in an amount of 0.01-15 wt % based on the total weight of the health food composition of the present invention, and the extract of the present invention may be added in an amount of 0.02-30 g, preferably 0.3-10 g, based on 100 ml of the health drink composition of the present invention.

The health drink composition of the present invention has no particular limitation on liquid components, except that it contains the extract as an essential component in the specified amount. The health beverage compositions of the present invention may additionally contain various sweetening agents or natural carbohydrates as in conventional beverages. Examples of the natural carbohydrates include monosaccharides, such as glucose and fructose, disaccharides, such as maltose and sucrose, polysaccharides, such as dextrin and cyclodextrin, and sugar alcohols, such as xylitol, sorbitol, and erythritol. In addition, flavors, including natural flavors (thaumatin and stevia extracts, e.g., rebaudioside A, glycyrrhizin, etc.) and synthetic flavors (saccharine, aspartame, etc.) may advantageously be used. The natural carbohydrates are generally added at a ratio of about 1-20 g, preferably about 5-12 g, per 100 ml of the composition of the present invention.

Aside from the above components, the composition of the present invention may contain various nutrients, vitamins, minerals (electrolytes), flavors such as synthetic flavors and natural flavors, coloring matter and enhancer (cheese, chocolate, etc.), pectic acid and its salts, alginic acid and its salts, organic acids, protective colloid thickeners, pH control agents, stabilizers, preservatives, glycerine, alcohols, carbonating agents for carbonated beverage use, and so on. In addition, the composition of the present invention may contain fruit fresh for the preparation of natural fruit juices, fruit juice beverages and vegetable beverages. These components can be used independently or in combination. The proportion of these additives is not so critical but can be generally selected from the range of 0 to about 20 parts by weight per 100 parts by weight of the composition of the present invention.

Further, because the composition containing the paprika extract of the present invention is based on natural materials, it has little or no toxicity and adverse effects, and thus can be used with safety for the purpose of prevention for a long period of time.

EXAMPLES

Hereinafter, the present invention will be described in further detail with reference to examples. It will be obvious to a person having ordinary skill in the art that these examples are illustrative purposes only and are not to be construed to limit the scope of the present invention.

Example 1

Preparation of Paprika Extract

Yellow, orange and red paprika plants which received GAP (Good Agricultural Practices) were purchased from a farming association corporation located in Iksan city, Jeollabuk-do, Korea.

First, paprika was washed clean with tap water and cut to a suitable size. The cut paprika pieces were squeezed into juice using a liquidizer in order to increase extraction efficiency. The obtained paprika juice and dregs were placed in a 1-L round bottom flask which was then connected to a 350-mm reflux condenser. While cold tap water was continuously allowed to flow into the reflux condenser, the round bottom flask containing the paprika juice and dregs was placed in a distiller at 80 and heated for 24 hours, thereby extracting concentrated paprika liquid.

The paprika extract obtained using the reflux condenser was filtered three times through filter paper having a diameter of 5 m to remove impurities other than the paprika extract. 25 ml of the filtered paprika extract was dispensed into each of 50-ml tubes and frozen rapidly using liquid nitrogen, and then kept in a deep freezer at −70° C. overnight (about 16 hours). In order to make the paprika into the form of powder, the paprika extract contained in the 50-ml tube was placed in a freeze drying container which was then connected to a freeze dryer, and it was freeze-dried for 5 days. After 5 days, the freeze-dried paprika extract powder was obtained (see FIG. 1).

Example 2

Construction of Asthma Mouse Model Using OVA 6-week-old female BALB/c mice were purchased from OrientBio Inc. All the mice were housed in a SPF (specific pathogen-free) state. All the animal experiments were approved by the Institutional Animal Care and Use Committee of Hanyang University and carried out according to an animal experiment guideline provided by the College of Medicine, Hanyang University.

A solution of 100 µg of OVA (ovalbumin; mouse inflammation inducer, Sigma) in 100 µl of PBS was mixed with 100 µl of aluminum hydroxide (immune response enhancer, 40 mg/ml; Pierce) for 30 minutes using two syringes. 200 µl of the obtained OVA/alum mixture was administered intraabdominally into mice at 7 days after the start of oral administration of the paprika extract, thereby inducing sensitization.

14 days after the first sensitization (experiment day 21), sensitization was induced once more. At experiment days 22, 23 and 24, a solution of 1.5 mg of OVA in 50 µl of PBS was injected intranasally into the mice by an animal anesthetic (PBS: Rompun: Zoletil 50=6:3:1), thereby making an asthma mouse model. In the case of the paprika group, the paprika extract powder was dissolved in saline at a concentration of µg/Kg and administered orally using a sonde once a day during the experiment period (0-24 days). In the case of the bodesonide group, bodesonide was injected intranasally into the mice at a concentration of 350 µg/ml at 1 hour before intranasal injection of OVA at days 22, 23 and 24. The bodesonide group, the control group and the asthma group were administered with saline at a concentration of 1 g/Kg once a day in the same manner as the paprika group.

Test Example 1

Change in Bodyweight of Mice

For the mice of the control and asthma group prepared in Example 2, the change in bodyweight caused by intake of the paprika extract was observed.

Figure 2:
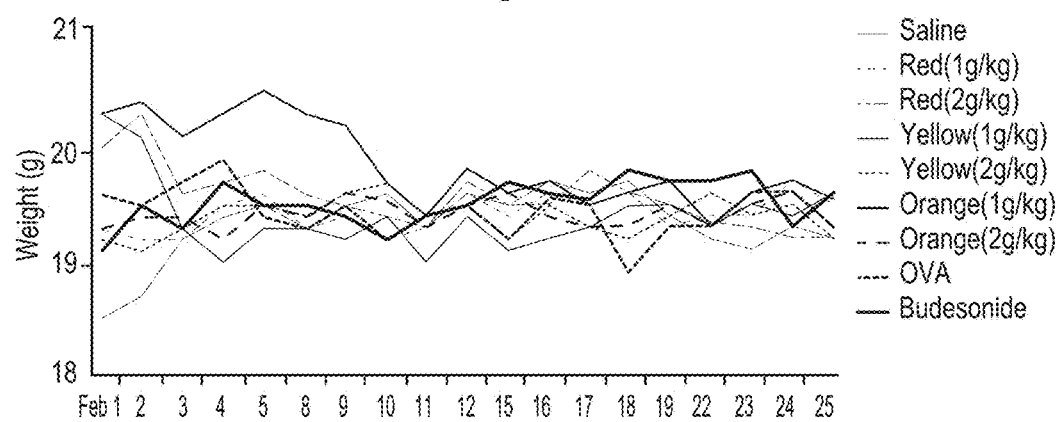
FIG. 2 is a graphic diagram showing the results of observation of changes in the bodyweights of a control group and test groups.

As a result, as can be seen in FIG. 2, the change in mouse bodyweight caused by intake of the paprika extract was not significant.

Example 3

Change in Number of Immune Cells 3-1: Extraction of Bronchial Alveolar Lavage Fluid (BAL Fluid) and Left Lung At 24 hours (experiment day 25) after experiment day 24 at which OVA was finally injected intranasally in Example 2, the mice were sacrificed for analysis. The mice were anesthetized with an animal anesthetic and then fixed to an anatomic plate. The diaphragm was removed, and blood was taken out from the left ventricle of the heart.

Then, the airway was secured and a catheter was inserted into the airway. A 1-ml syringe containing 1 ml of PBS was connected to the catheter, and the plunger of the syringe was pushed slowly and then pulled, after which the syringe was placed in a 1.5-ml tube. This process was repeated once more, thereby obtaining 2 ml of bronchial alveolar lavage fluid. 2 ml of PBS was allowed to flow through the left ventricle of the heart to wash the lungs. The lungs were extracted by incision, and for tissue staining, the left lung tissue was fixed in 4 ml of 10% neutral buffered formalin (NBF).

3-2: Change in the Number of Immune Cells in Bronchial Alveolar Lavage Fluid 2 ml of the bronchial alveolar lavage fluid obtained from each of the mice was centrifuged at 3000 rpm at 4° C. for 20 minutes to settle down immune cells present in the bronchial alveolar lavage fluid. The supernatant was removed while the settled cells. 100 µl of PBS was added to the tube from which the supernatant has been removed to leave the immune cells, and the cells were suspended.

To count the cell number, 100 µl of PBS containing 10 µl of the immune cells was mixed with 90 µl of the cell staining reagent Trypan blue. 10 µl of the mixture was taken and placed on a hemacytometer slide, after which the total number of the immune cells was counted with an optical microscope.

Figure 3:
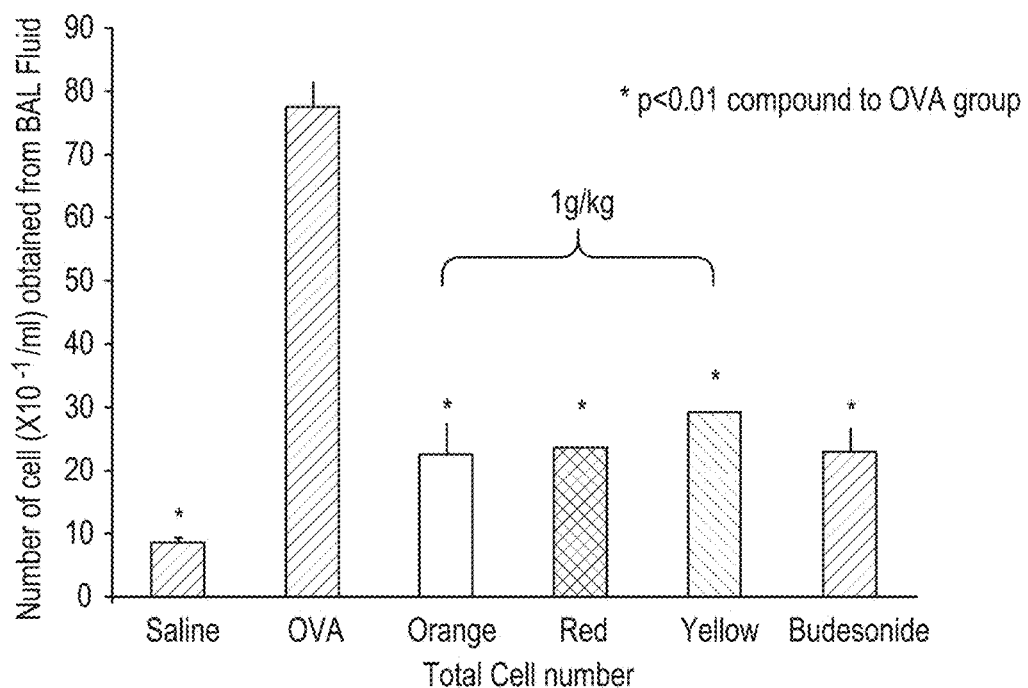
FIG. 3 shows the results of observation of changes in the total number of cells in mice of a control group and test groups.
Figure 4:
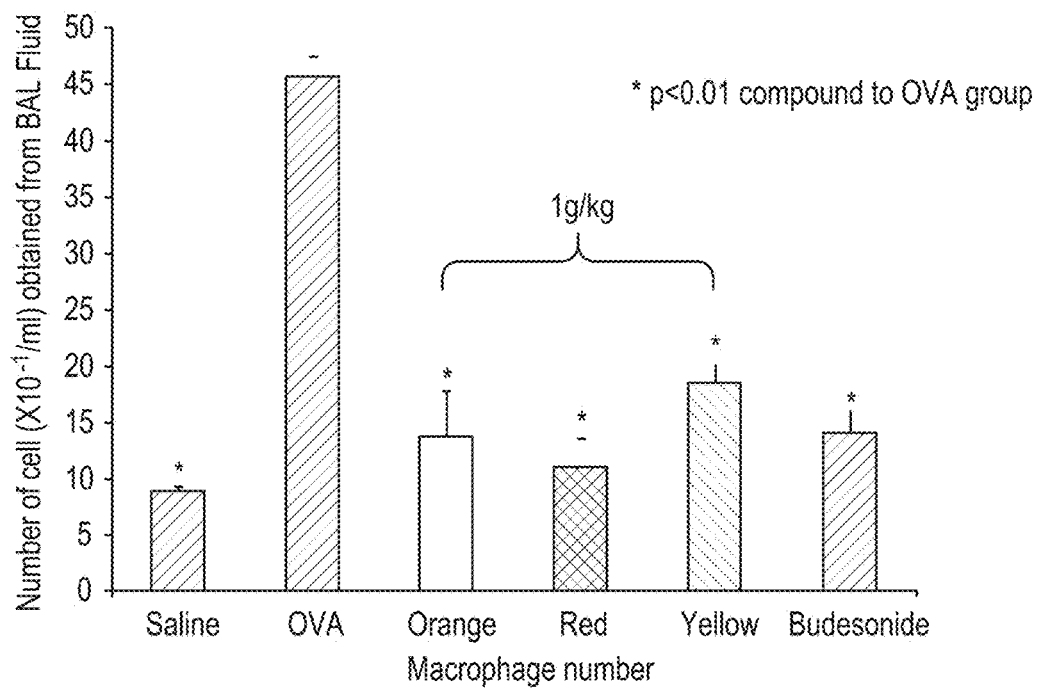
FIG. 4 shows the results of observation of changes in the number of macrophages in mice of a control group and test groups.
Figure 5:
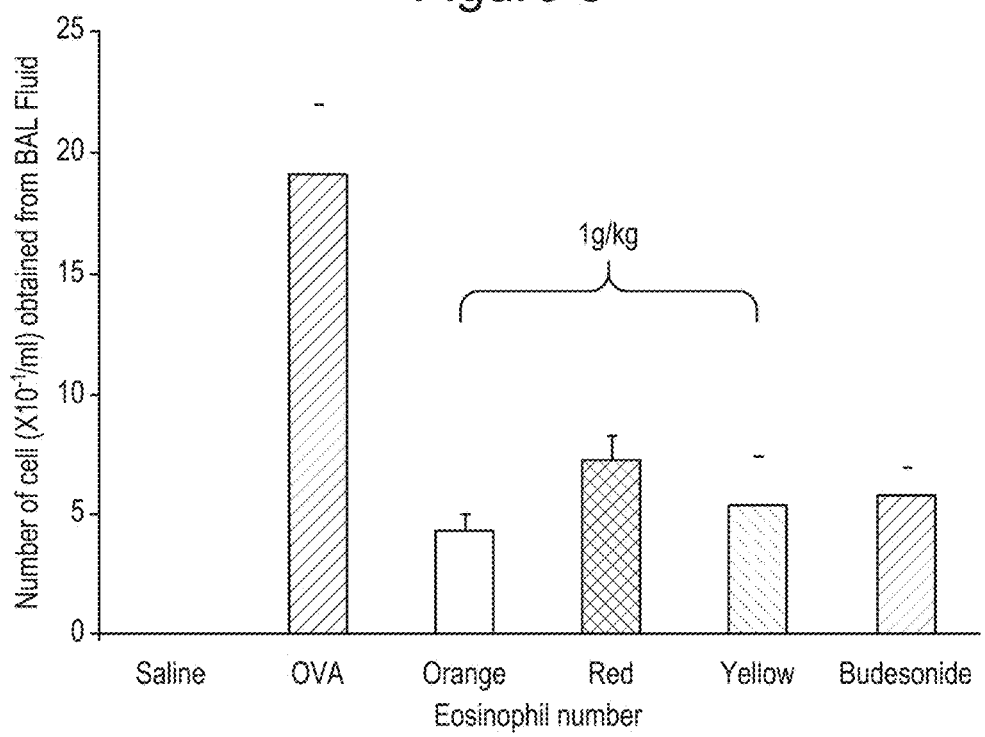
FIG. 5 shows the results of observation of changes in the number of eosinophils in mice of a control group and test groups.
Figure 6:
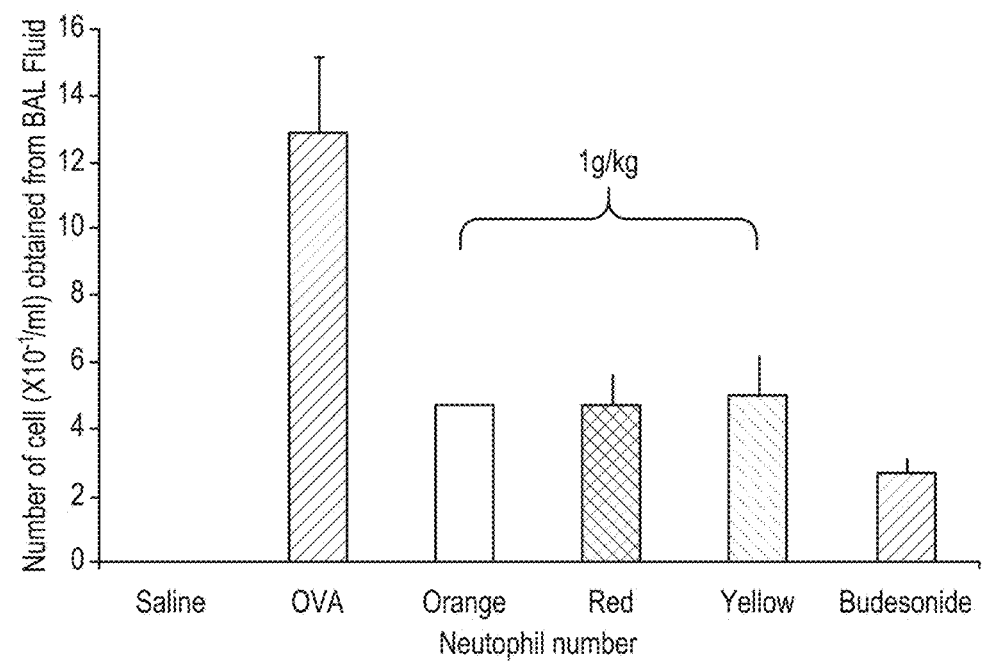
FIG. 6 shows the results of observation of changes in the number of neutrophils in mice of a control group and test groups.
Figure 7:
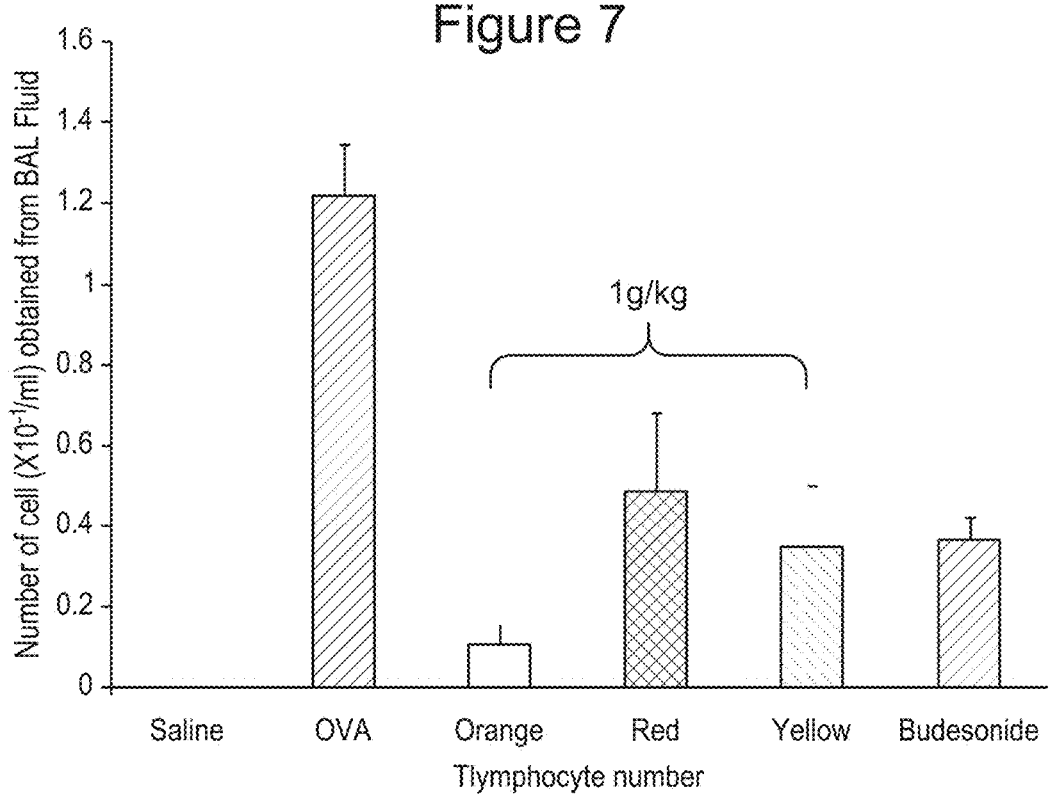
FIG. 7 shows the results of observation of changes in the number of T lymphocytes in mice of a control group and test groups.

The results of the cell counting are shown in FIG. 3.

As can be seen in FIG. 3, the mice administered with the paprika extract showed a significant decrease (about 70%) in the total cell number compared to the asthma mouse model [Saline—normal mice; OVA—asthma-induced mice; Orange, Red, Yellow—paprika extract; budesonide—control]. In other words, it was shown that the total cell number of the mice administered with the paprika extract was significantly reduced close to that of the normal mouse group. Herein, the closer the total cell number, the better is the therapeutic effect.

After completion of the counting of the total immune cell number, the immune cells in PBS were diluted in 90 µl of PBS so that the immune cell number reached 100, and 90 µl of the cell dilution was placed into each hole of a cytospin device equipped with a slide. The cell dilution was centrifuged at 1000 rpm for 5 minutes, and the slide was separated. The cells on the slide were dried, and then the immune cells were stained using a Diff-quik staining kit, and one drop of mount solution was added thereto. Then, the slide was covered with a cover glass. The numbers of the stained macrophages, eosinophils, neutrophils and T lymphocytes were counted with an optical microscope.

The results of the cell counting are shown in FIGS. 4 to 7, respectively.

The number of the macrophages obtained from the bronchial alveolar lavage fluid was compared between the test groups. As a result, it was shown that the mice administered with the paprika extract showed a significant decrease in the total cell number compared to the asthma mouse model (orange—70%, red—74%, yellow—60%) (see FIG. 4).

Also, the number of the eosinophils obtained from the bronchial alveolar lavage fluid was compared between the test groups. As a result, it was shown that the mice administered with the paprika extract showed a significant decrease in the total cell number compared to the asthma mouse model (orange-78%, red—63%, yellow—73%) (see FIG. 5).

Furthermore, the number of the neutrophils obtained from the bronchial alveolar lavage fluid was compared between the test groups. As a result, it was shown that the mice administered with the paprika extract showed a significant decrease in the total cell number compared to the asthma mouse model (orange—64%, red—64%, yellow—72%) (see FIG. 6).

In addition, the number of the T-lymphocytes obtained from the bronchial alveolar lavage fluid was compared between the test groups. As a result, it was shown that the mice administered with the paprika extract showed a significant decrease in the total cell number compared to the asthma mouse model (orange—90%, red—60%, yellow—70%) (see FIG. 7).

Figure 8:
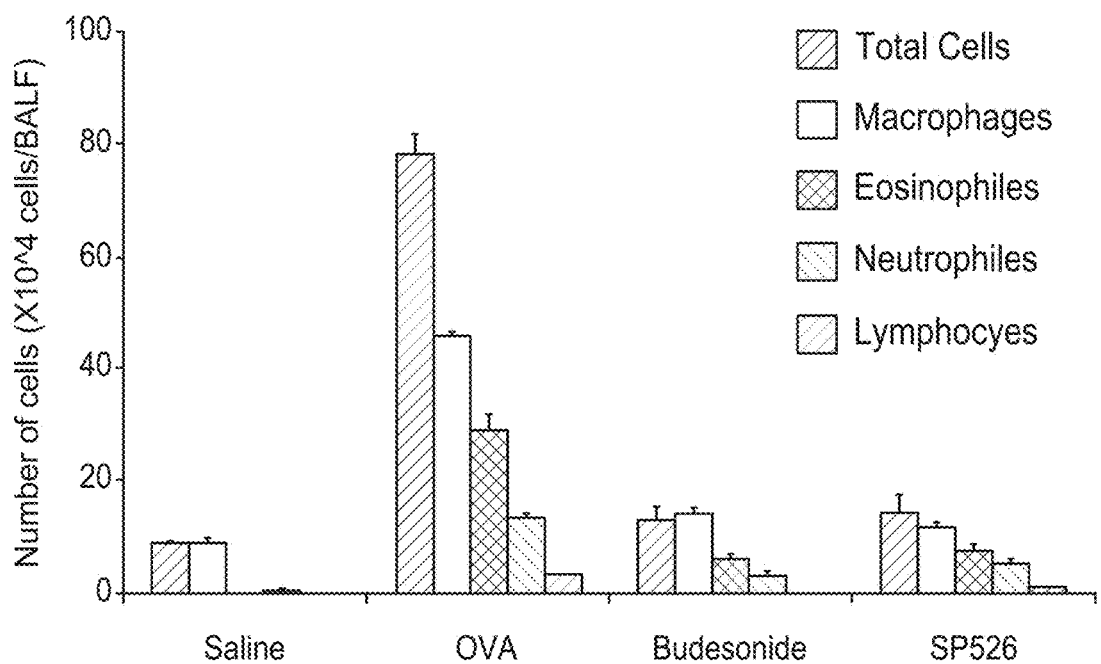
FIG. 8 collectively shows the results shown in FIGS. 3 to 7.

FIG. 8 is a graph collectively showing the results shown in FIGS. 3 to 7. As can be seen therein, the induction of asthma in the mice administered with the paprika extract was inhibited, and thus the mice administered with the paprika extract showed the normal immune cell number, like the mice treated with budesonide or the control Sham (PBS) mice.

In other words, the above results revealed that the paprika extract of the present invention has the effect of ameliorating asthma disease by reducing the number of various immune cells.

Example 4

Tissue PAS Staining

The left lung extracted from the mice in Example 3 was fixed in 10% formalin solution for 72 hours, and then the tissue was washed with running tap water overnight (about 16 hours).

The tissue was placed in 70% ethanol for 1 hour and 100% ethanol for 50 minutes, and then placed twice in a 1:1 mixture of xylene and 100% ethanol for 30 minutes each time and in 100% xylene for 40 minutes each time. Then, the tissue was placed twice in a 1:1 mixture of paraffin and xylene for 40 minutes each time and in 100% paraffin for 40 minutes each time. After these dehydration, clearing and paraffin infiltration processes, the tissue was embedded to prepare a paraffin block.

The prepared paraffin block was sectioned to a thickness of 3 m using a microtome (Leica). The sectioned tissue was deparaffinized with xylene, hydrated with ethanol, washed with tap water, and dipped three times in 0.5% periodic acid (JUNSEI) aqueous solution for 10 minutes each time, tap water for 5 minutes each time, Schiff reagent (Sigma-Aldrich) for 10 minutes each time, rap water for 10 minutes each time, and sulfite (JUNSEI) rinse for 2 minutes each time. Then, the tissue was dipped 2-3 times in Harris hematoxylin solution (Sigma-Aldrich) for 3 minutes each time, tap water for 5 minutes, and 1% HCL-alcohol, and washed with tap water. After the tissue has been dried, one drop of balsam was added to the tissue which was then mounted. The stained tissue was observed with an optical microscope.

Figure 9:
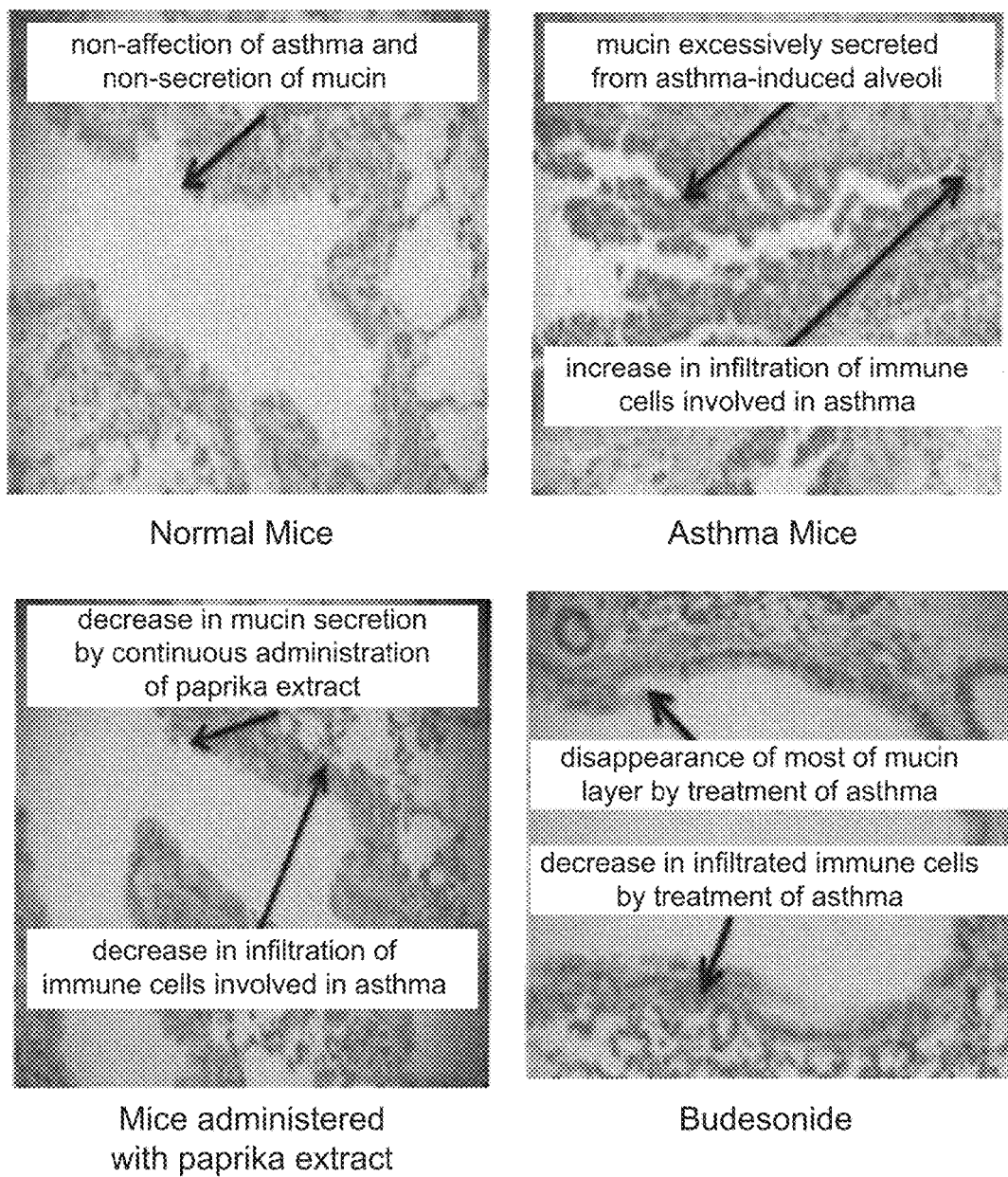
FIG. 9 is a set of micrographs showing the infiltration of mucin and immune cells in mice of a control group and test groups.

As can be seen that FIG. 9, the mice administered with the paprika extract showed a significant decrease in the infiltration of mucin and immune cells compared to the asthma mouse model.

Example 5

Measurement of Immunoglobulin E(IgE) Level

When asthma in mice is induced using OVA, the immunoglobulin-E (IgE) among the blood antibody levels of the mice increases in proportion to the severity of asthma. Based on this principle, the paprika extract obtained according to the method of Example 1 was named "sample SP526", and the blood immunoglobulin-E (IgE) level of the mice was measured.

Figure 10:
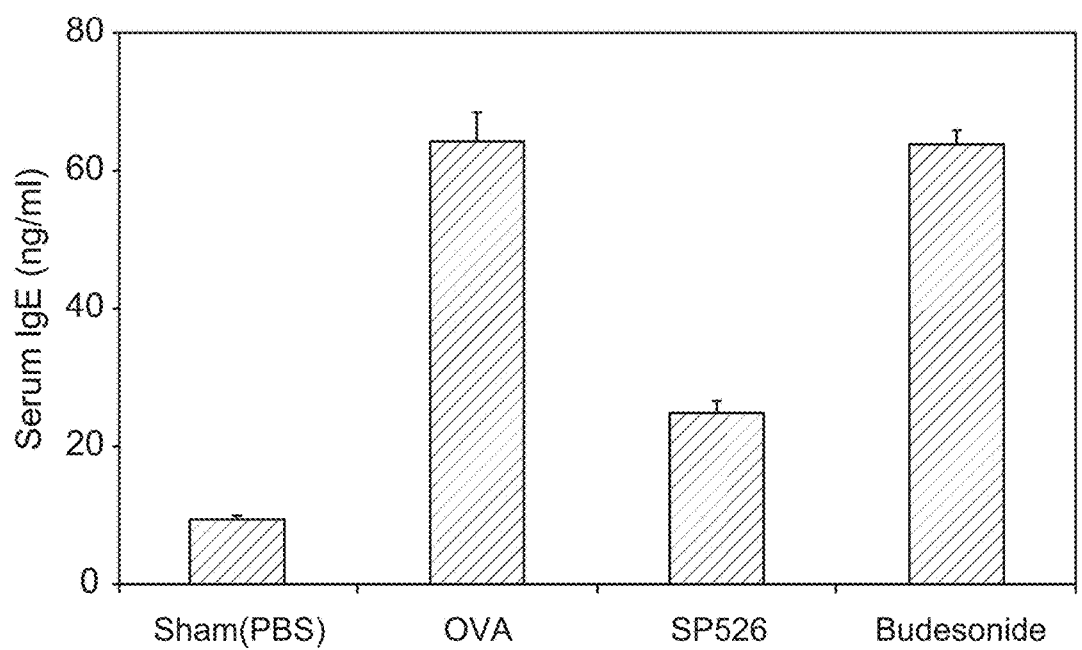
FIG. 10 is a graph showing the results of measurement of blood immunoglobulin-E (IgE) levels.

The results of the measurement are shown in FIG. 10. As can be seen therein, the IgE levels of the mice administered with the red paprika extract were about 70% lower than those of the asthma-induced mice (OVA) ($P<0.01$).

Meanwhile, immunoglobulin IgG2a is produced by activation of Th1 cells, and the activity of Th1 cells reduces the level of IgG1 which is increased by the activity of Th2 cells. Thus, IgG1 and IgG2a were analyzed.

Figure 11:
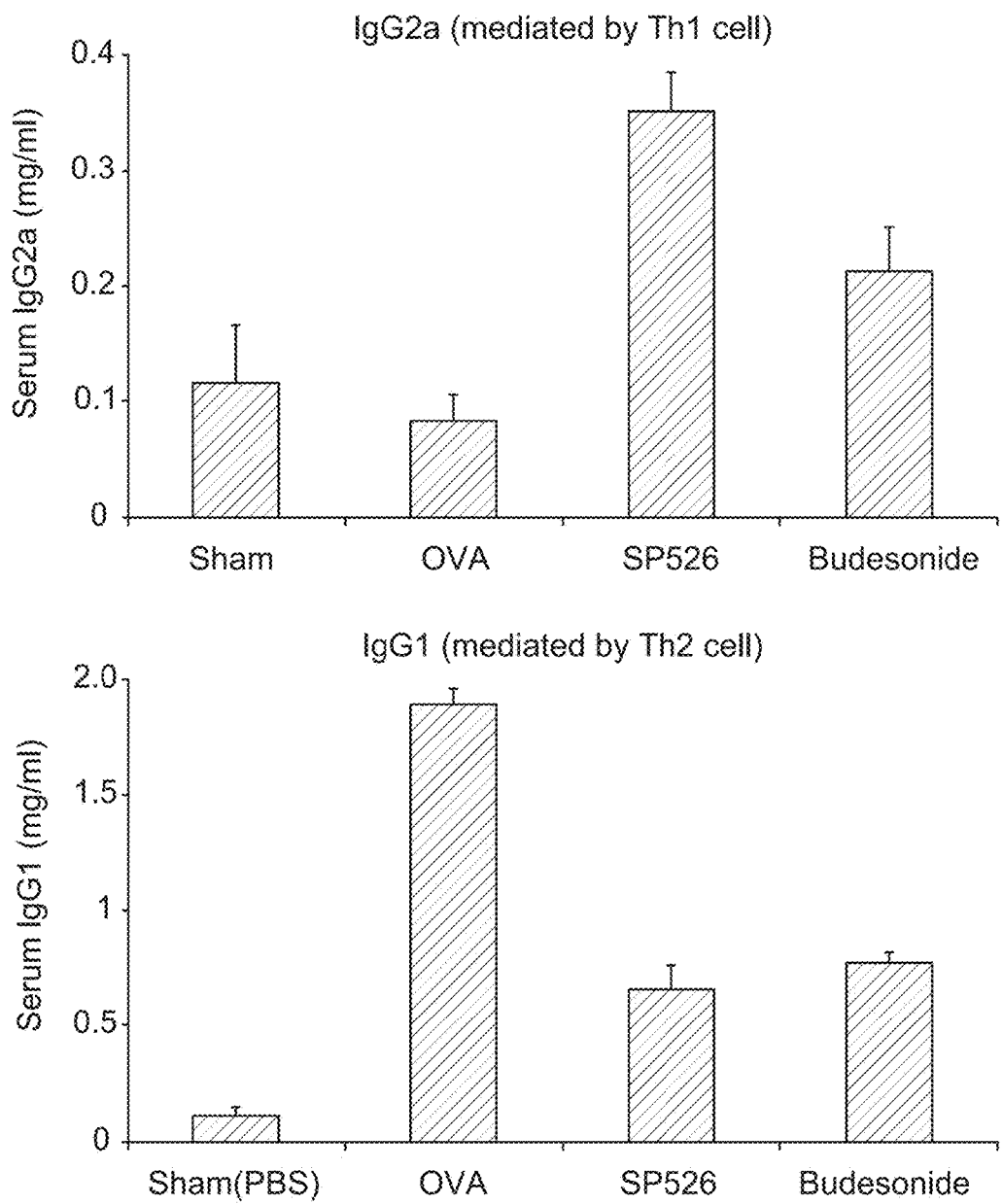
FIG. 11 is a set of graph showing the results of measurement of blood IgG1 and IgG2a levels.

As a result, it was shown that the level of IgG1 increased in the OVA-induced mice and the expression of IgG1 did not increase in the control mice and the budesonide-treated mice (see FIG. 11). In addition, the level of IgG2a in the mice administered with the red paprika extract was about 70% higher than that in the asthma-induced mice (OVA) (*$P<0.01$).

Comparative Example 1

Comparison with Luteolin in Asthma Model

In order to examine whether the asthma inhibitory effect of the paprika extract of the present invention is attributable to a combination of components or a specific component alone, the following test was carried out.

Figure 12:
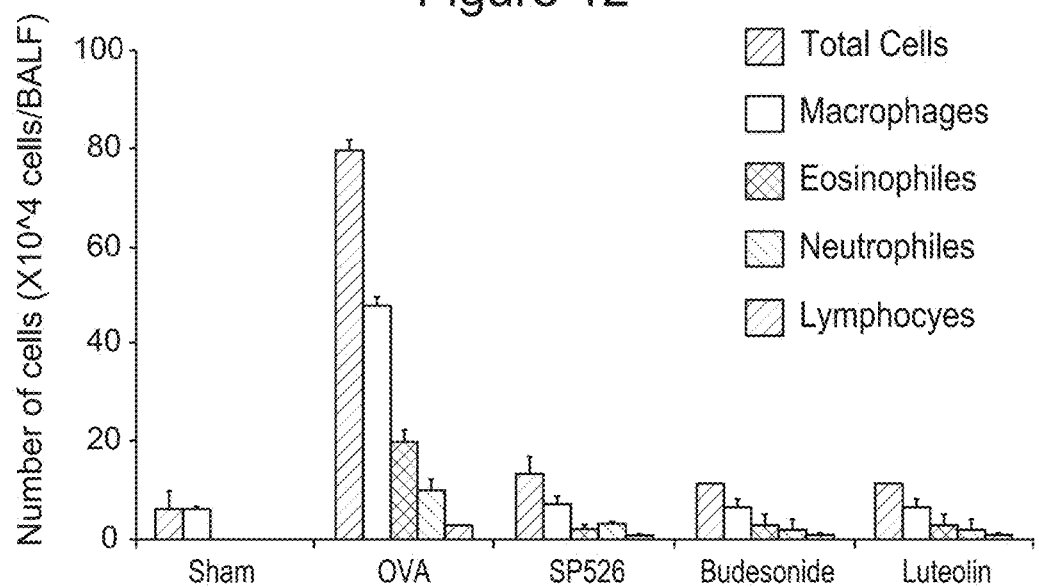
FIG. 12 shows the results of examining the immune cell infiltration of luteolin.

Specifically, the immune cell infiltration of luteolin was examined. As a result, it was shown that luteolin inhibited the infiltration of immune cells, like budesonide (see FIG. 12).

Figure 13:
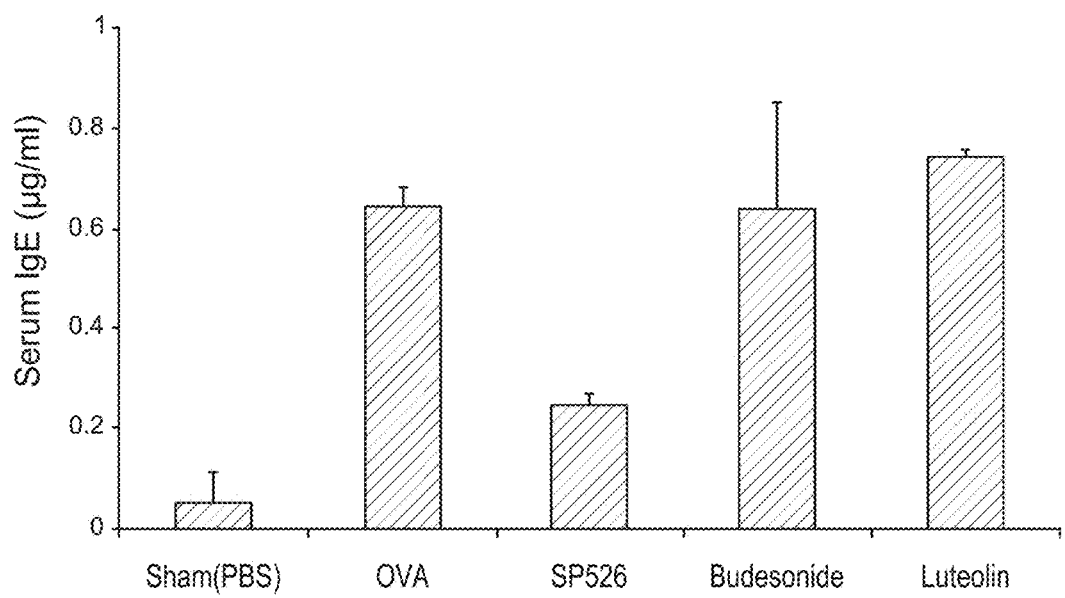
FIG. 13 shows the results of measurement of immunoglobulin-E (IgE) levels which resulted when luteolin was used.

Also, the level of immunoglobulin-E (IgE) was measured. The results of the measurement indicated that luteolin did not reduce blood immunoglobulin-E levels, like budesonide (see FIG. 13).

Figure 14:
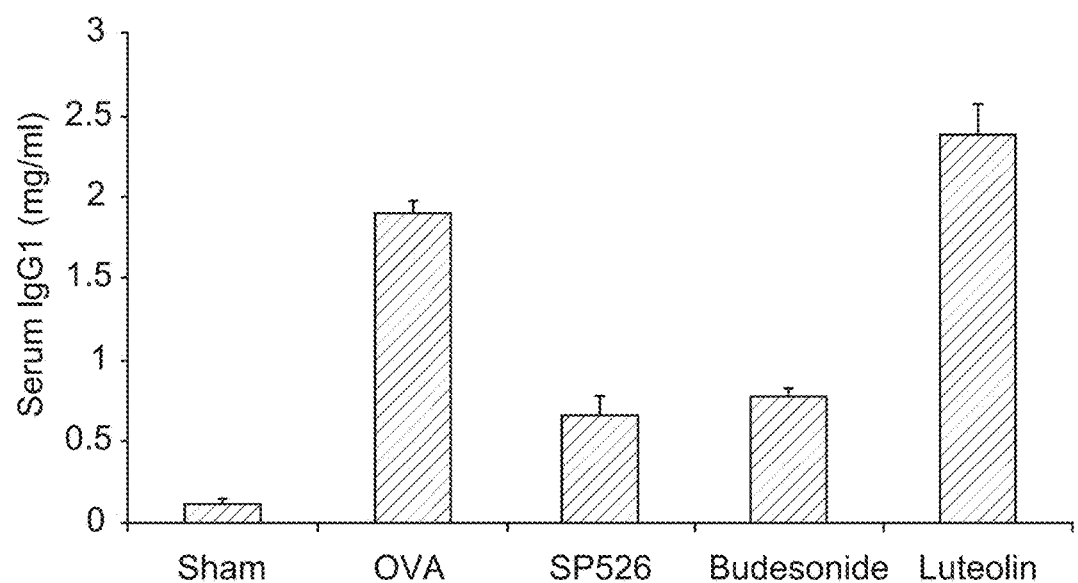
FIG. 14 shows the results of measurement of IgG1 and IgG2a levels which resulted when luteolin was used.
Figure 14:
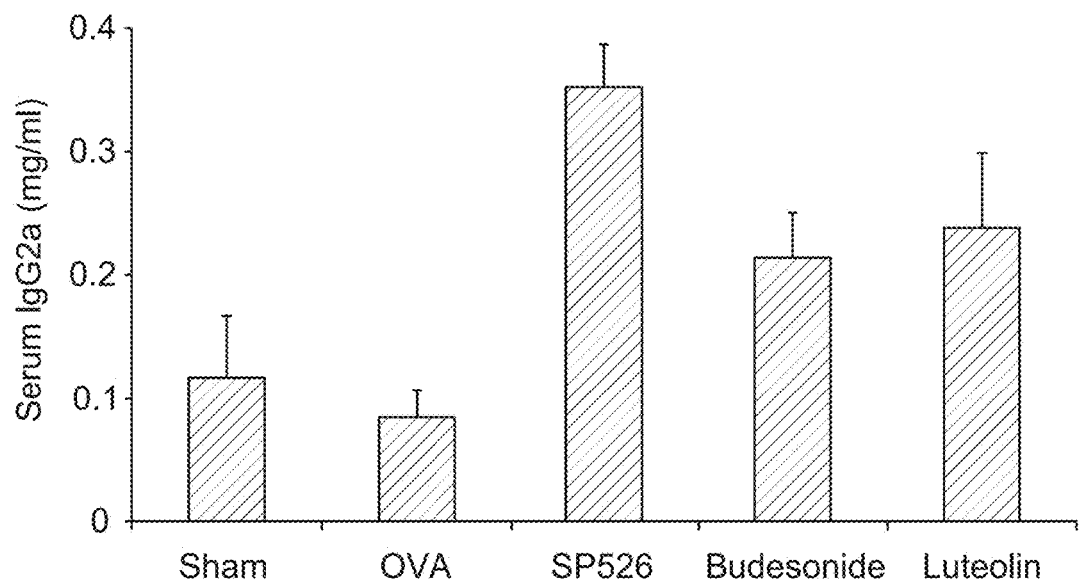

In addition, the results of analysis of IgG1 and IgG2a indicated that the expression of immunoglobulin IgG1 caused by the activation of Th2 was not inhibited in the luteolin-treated mice and that luteolin produced IgG2a, which is an index of the activation of Th1 cells, thereby relieving asthma (see FIG. 14).

Such results suggest that luteolin shows the same effect as budesonide which has been used as an asthma-relieving agent. Thus, in this experiment, budesonide was used as a control, and the effect of budesonide means the effect of luteolin.

In other words, because luteolin alone shows an excellent effect of inhibiting asthma, the significant effect of the use of the inventive paprika extract can be said to be an effect attributable to a combination of various components present in the paprika extract.

Example 6

Measurement of Cytokines IL-4, IL-13

IL-4 and IL-13 are immune signaling substances (cytokines) which are secreted from the immune cells of mice affected with asthma, increases in the amounts thereof indicate an increase in the severity of asthma.

(1) Concanavalin a (ConA) Stimulation

Thus, immune cells obtained by spleen homogenization were exposed to the non-specific stimulus concanavalin A for a predetermined time (12 hours), and the levels of cytokines secreted from the immune cells were measured, thereby determining immune responses.

Figure 15:
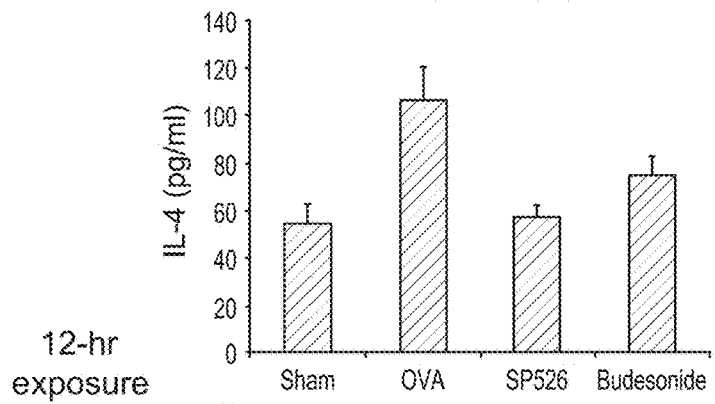
FIG. 15 shows the results of observing immune responses by measuring the concentrations of cytokines secreted upon exposure to ConA.
Figure 15:
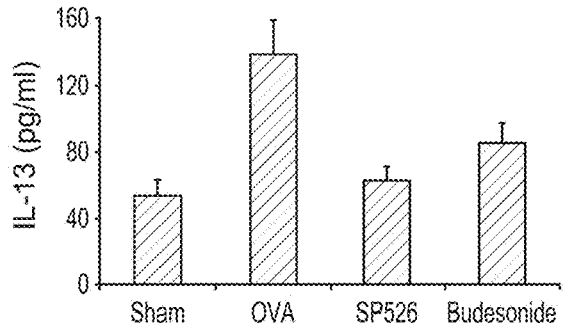
Figure 15:
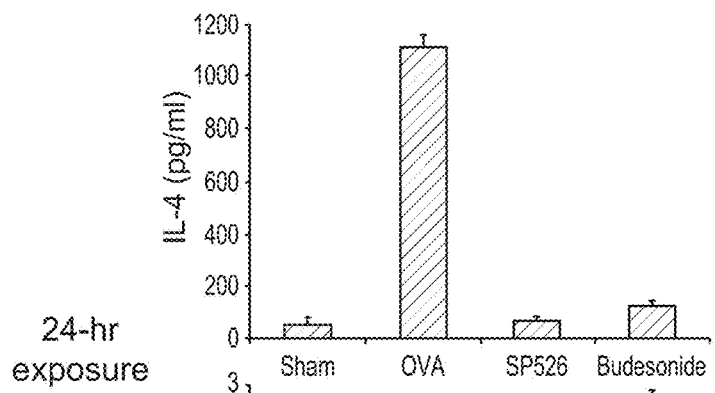
Figure 15:
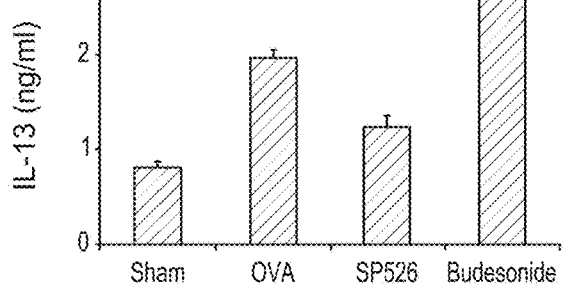

The results of measurement of cytokines (IL-4 and IL-13) secreted from the spleen cells stimulated with ConA are shown in FIG. 15. As can be seen therein, the level of IL-4 secreted from the immune cells of the mice administered with the red paprika extract was as significantly low as about 50% and was similar to that of the normal mice. In addition, the level of IL-13 secreted from the immune cells of the mice administered with the red paprika extract was as low as about 50% of that of the asthma-induced mice and was similar to that of the normal mice.

Further, the level of IL-4 from the spleen cells stimulated for 48 hours did significantly differ from that the level of IL-4 from the spleen cells stimulated for 12 hours. However, stimulation for 48 hours induced the stimulation of non-activated cells, and thus the difference in IL-13 between 12-hr stimulation and 48-hr stimulation was insignificant.

(2) Stimulation with Asthma Inducer Ovalbumin (OVA)

In addition, immune cells obtained by spleen homogenization were exposed to the asthma inducer ovalbumin (OVA) for a predetermined time (12 hours), and the levels of cytokines secreted from the immune cells were measured, thereby determining immune responses.

Figure 16:
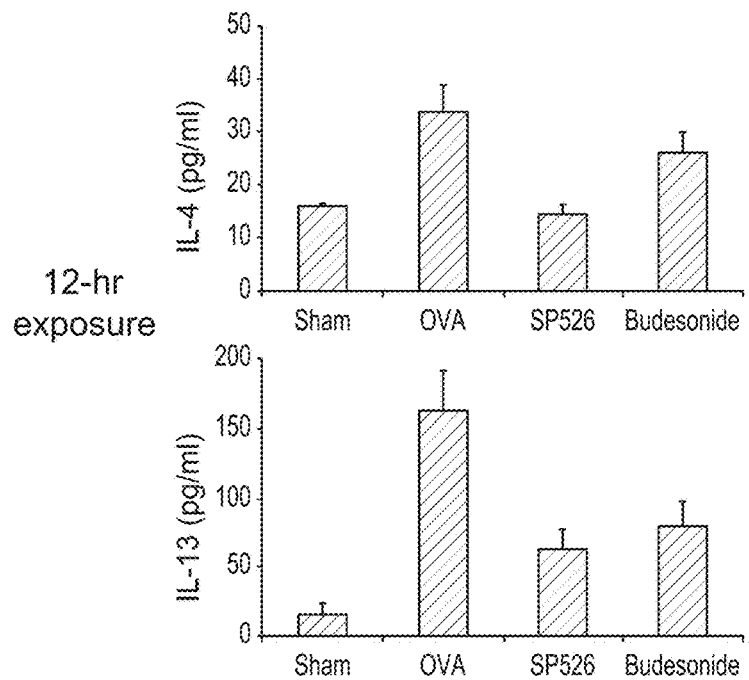
FIG. 16 shows the results of observing immune responses by measuring the concentrations of cytokines secreted upon exposure to OVA.
Figure 16:
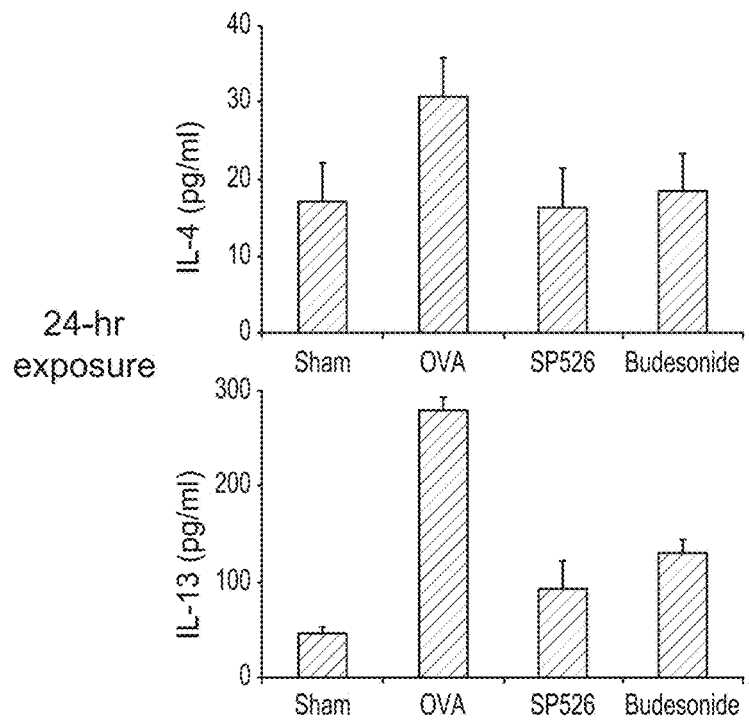

The results of measurement of cytokines (IL-4 and IL-13) secreted from the spleen cells stimulated with OVA are shown in FIG. 16.

Specifically, the level of IL-4 secreted from the immune cells of the mice administered with the red paprika extract was reduced by about 50% and was similar to that from the normal mice, and the level of IL-13 secreted from the immune cells of the mice administered with the red paprika extract was reduced by about 60% compared to that from the asthma induced mice. A decrease in the IL-13 level influences Mucin5AC gene expression and airway hypersensitivity.

In addition, in the case of the spleen cells stimulated with OVA, the level of IL-4 did significantly differ between 12-hr stimulation and 48-hr stimulation, and the expression of IL-13 in 48-hr stimulation was reduced by about 80% ($p<0.01$). In other words, it could be seen that the expressions of IL-4 and IL-13 by stimulation with the asthma inducer OVA were significantly reduced by the red paprika extract.

Figure 17:
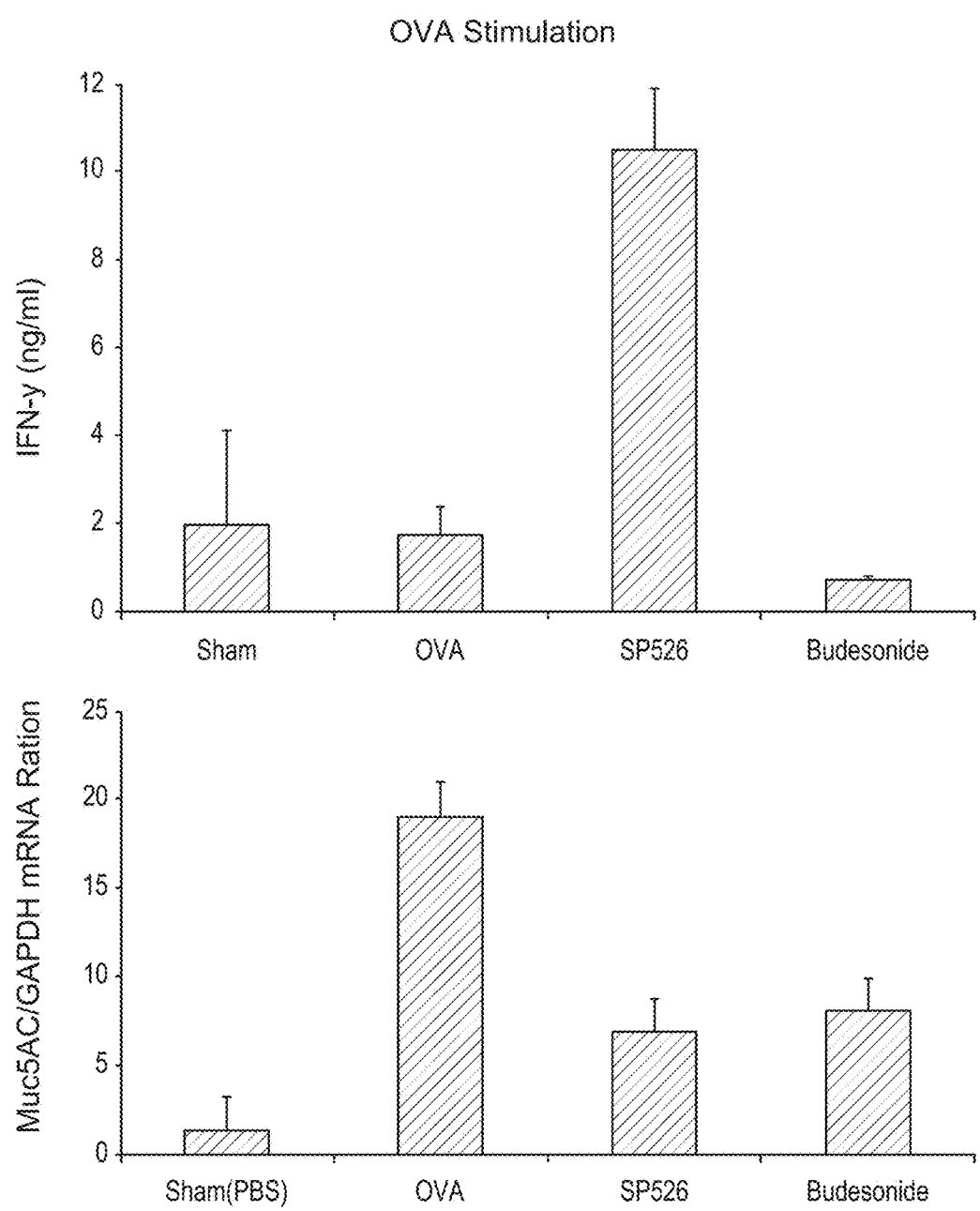
FIG. 17 shows the results of measuring the amount of the TH1 cytokine IFN-gamma after stimulation with OVA.

In addition, after 48-hr stimulation with OVA, the amount of the TH1 cytokine IFN-gamma was measured. The results of the measurement indicated that the production of IFN-gamma in the mice administered with the red paprika extract (SP526) was about 5 times increased (see FIG. 17, $P<0.01$). Such results suggest that, in the case of the mice administered with the paprika extract, Th1 immune responses against OVA could be induced.

Example 7

Measurement of Mucin Secretion

The condition of asthma can be determined by measuring the degree of secretion of mucin from bronchial alveolar epithelial cells, and the degree of secretion of mucin can be determined by the relative concentration of mucin messenger RNA (m-RNA) in bronchial alveolar epithelial cells.

Thus, the relative concentration of m-RNA (mucin gene m-RNA) in bronchial alveolar epithelial cells was measured using real time-PCR.

Figure 18:
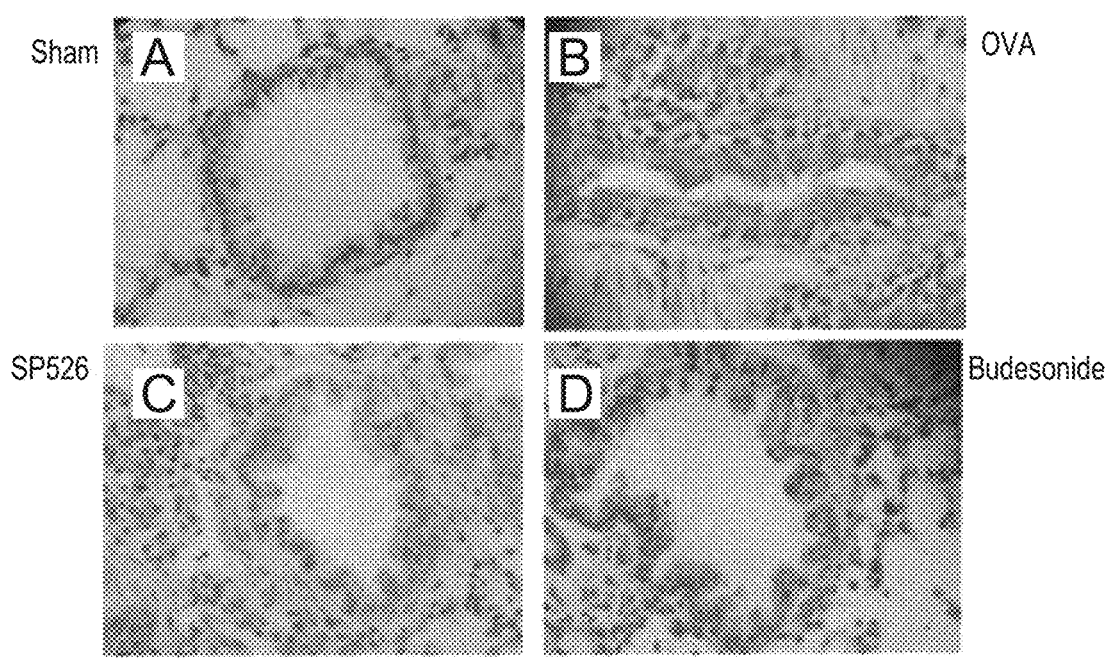
FIG. 18 shows the results of measuring the relative concentration of bronchial alveolar epithelial cell m-RNA (mucin gene m-RNA).

As a result, as can be seen in FIG. 18, the relative concentration of mucin m-RNA in the mice administered with the red paprika extract was about 80% lower than that in the asthma-induced mice.

Figure 19:
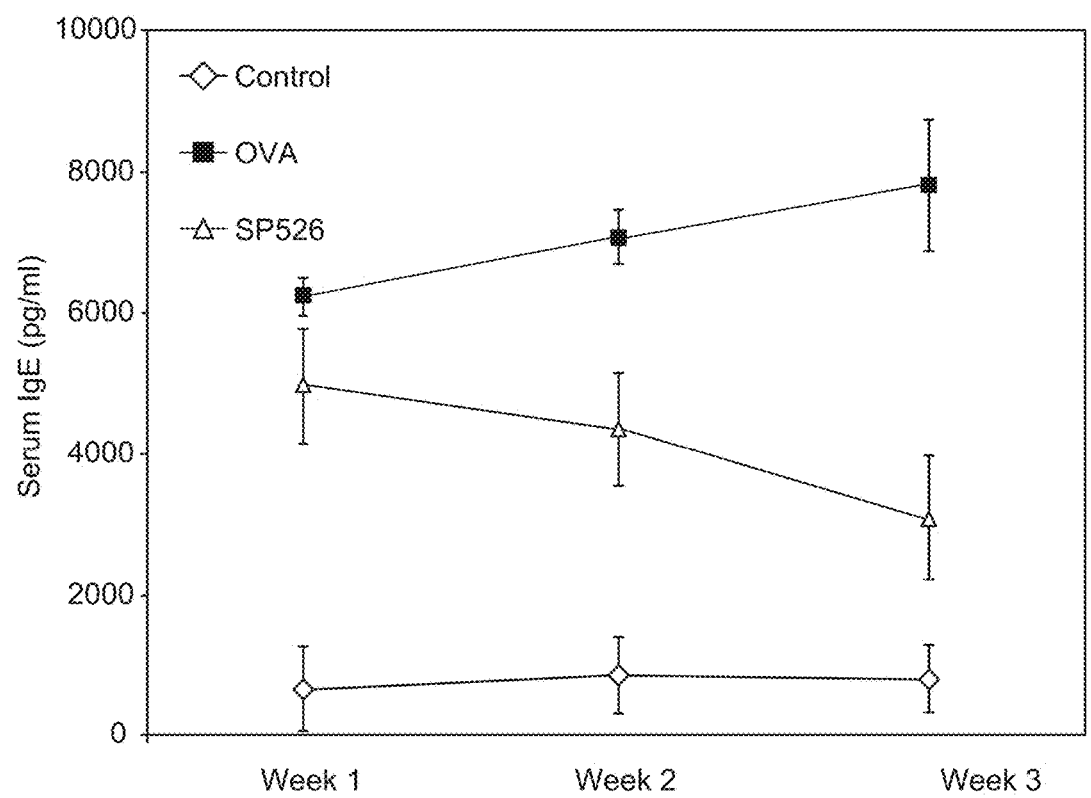
FIG. 19 is a set of micrographs of stained lung tissues of test groups.

In addition, the lung tissues of the test groups were stained and observed with a microscope. As a result, it was shown that the infiltration ofmucin and immune cells in the mice administered with the paprika extract was significantly decreased compared to that in the asthma-induced mice (see FIG. 19).

Example 8

Chronic Asthma Disease

Figure 20:
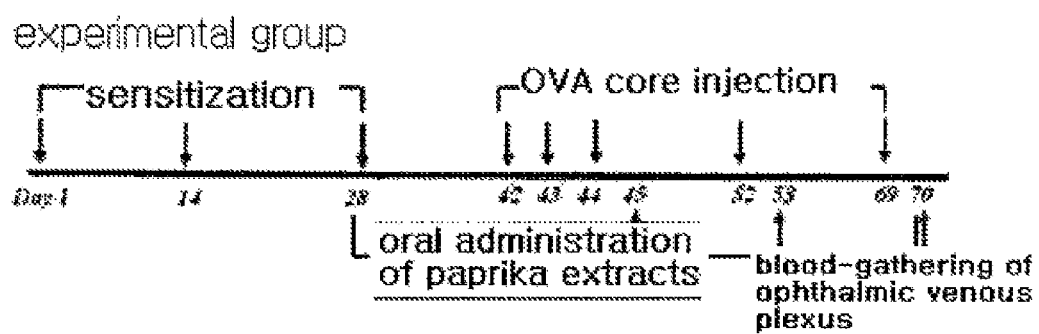
FIG. 20 is a diagram showing the experimental protocol for Example 8.

The effect of administration of the inventive paprika extract in a chronic mouse model was examined as a function of time (as shown in FIG. 20).

Figure 21:
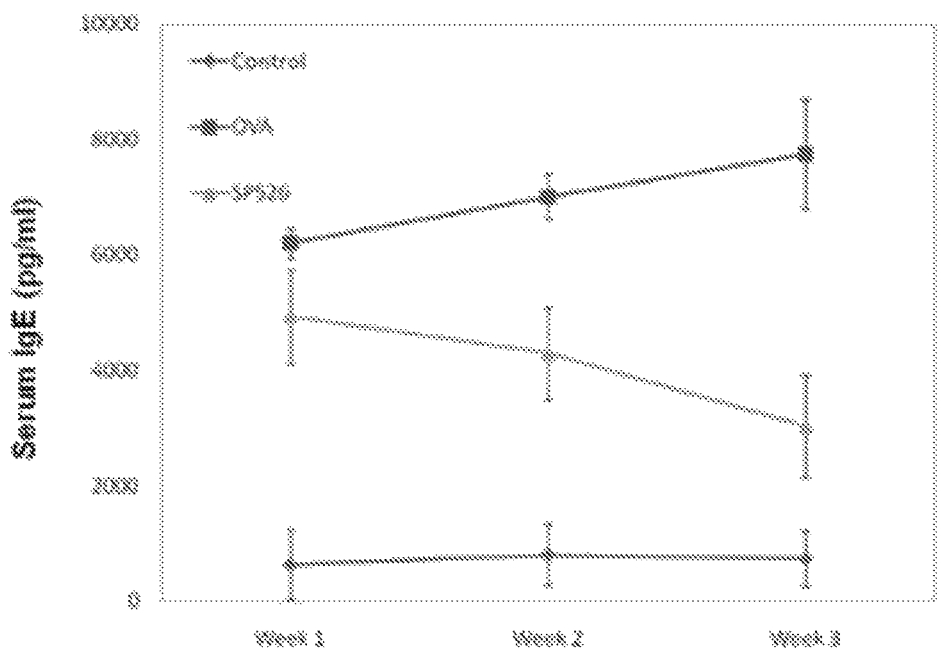
FIG. 21 is a graph showing the results of examining the effects of the paprika extract of the present invention in a chronic rat model as a function of time.

As a result, as can be seen in FIG. 21, administration of the paprika extract induced a decrease in the level of immunoglobulin E. This effect suggests that administration of the paprika extract changes an immune response to Th1 even after the development of asthma, thereby relieving asthma.

The invention claimed is:

1. A method of treating or reducing the incidence of asthma disease, comprising administering to a patient in need thereof a pharmaceutical composition including a paprika extract as an active ingredient, wherein the paprika is *Capsicum annuum* var. *angulosum*.

2. The method of claim 1, wherein the extract is a crude extract, polar solvent-soluble extract or non-polar solvent-soluble extract of paprika.

3. The method of claim 2, wherein the crude extract is an extract solubilized in a solvent selected from among water, including purified water, methanol, ethanol, butanol, and mixed solvents thereof.

4. The method of claim 2, wherein the polar solvent-soluble extract comprises an extract solubilized in a solvent selected from among water, ethanol, butanol, and mixed solvents thereof.

5. The method of claim 2, wherein the non-polar solvent-soluble extract comprises an extract solubilized in hexane, chloroform, dichloromethane or ethyl acetate.

6. The method of claim 1, wherein the content of the paprika extract in the composition is 0.1-50 wt% based on the total weight of the composition.

7. The method of claim 1, wherein the paprika is selected from the group consisting of paprikas which are green, orange, yellow and red in color.

8. The method of claim 1, wherein the method treats an asthma disease.

* * * * *